United States Patent [19]

Futatsugi et al.

[11] Patent Number: 4,727,428
[45] Date of Patent: Feb. 23, 1988

[54] METHOD AND APPARATUS FOR COMPENSATION OF LED-ARRAY OUTPUT POWER VARIATION IN ELECTROPHOTOGRAPHIC PRINTING

[75] Inventors: Kiyoshi Futatsugi; Inui Yasuo; Mitsuo Mochizuki, all of Tokyo; Akira Hichijou, Yokohama, all of Japan

[73] Assignee: Matsushita Graphic Communication Systems, Inc., Tokyo, Japan

[21] Appl. No.: 937,623

[22] Filed: Dec. 1, 1986

[30] Foreign Application Priority Data

Dec. 4, 1985 [JP] Japan .................... 60-272729

[51] Int. Cl.[4] .......... H04N 1/21; H04N 1/23; G01D 9/42; G01D 15/14
[52] U.S. Cl. ................... 358/296; 358/302; 346/107 R; 346/160
[58] Field of Search ............ 358/280, 283, 285, 296, 358/298, 300, 302; 346/107 R, 160; 250/205

[56] References Cited

U.S. PATENT DOCUMENTS

| | | | |
|---|---|---|---|
| 4,455,562 | 6/1984 | Dolan et al. | 346/160 |
| 4,563,747 | 1/1986 | Tidd | 358/296 X |
| 4,596,995 | 6/1986 | Yamakawa et al. | 358/302 X |

FOREIGN PATENT DOCUMENTS

47556  3/1985  Japan .................... 358/296

Primary Examiner—E. A. Goldberg
Assistant Examiner—Patrick W. Foster
Attorney, Agent, or Firm—Wenderoth, Lind & Ponack

[57] ABSTRACT

In a method and an apparatus for compensation of any variation that occurs in the output power or luminous energy of a LED array used in electrophotographic printing, the time for applying a current to one line of the LED array is optimally divided into a fundamental on-time for constant current application to the individual elements of the LED array and a compensational on-time for selective current application thereto in such a manner that the exposure values on a photosensitive medium become uniform.

10 Claims, 8 Drawing Figures

METHOD AND APPARATUS FOR COMPENSATION OF LED-ARRAY OUTPUT POWER VARIATION IN ELECTROPHOTOGRAPHIC PRINTING

BACKGROUND OF THE INVENTION

1. Field of the Invention

The present invention relates to a method and an apparatus for compensation of any variation that occurs in the output power or luminous energy of an LED (light emitting diode) array in an LED array head used for writing in an electrophotographic optical printer.

2. Description of the Prior Art

With the recent enhancement attained in the processing capabilities of OA (office automation) apparatus, it is conspicuous that the demand for high-resolution fast recording apparatus such as optical printer is remarkably increasing. In particular, studies are in rapid progress with regard to an optical writing system employing a full solid-state head with an LED array, liquid-crystal shutter array or the like, so as to realize an extremely compact, lightweight and low-cost structure. Although such apparatus has some merits including adaptability to mass production, high reliability and facility for maintenance, there also exists a problem peculiar to an array light source that individual elements thereof are not free from performance variation.

Generally in an LED array head, there is adopted a means of covering a print area by arranging a multiplicity of monolithic LED array chips each composed of integrated 64 to 256 elements. And in the light source for an optical printer, the output power or luminous energy of each light emitting element needs to be substantially the same.

In the present technical stage, however, it is unavoidable that some performance variation is induced among the elements due to the defects in commercially available wafers or because of nonuniformity in the process of production. And such output power variation in the LED array eventually brings about nonuniform diameters of printed dots. It is therefore essential to compensate such variation in the optical writing system using an LED array head.

With regard to compensation of LED-array output power variation, the following two methods have been known heretofore.

(1) A technique of connecting series resistors of mutually different resistance values to the individual elements respectively and driving them at a constant voltage. (Compensation by hardware)

(2) A technique of controlling a current application on-time for each of the elements so that the exposure values thereof become uniform on a photosensitive medium. (Compensation by software)

According to the former method, the circuit configuration needs to be such that currents flowing in the individual elements of different luminous energies are changeable. And another disadvantage is that once the circuit is set, it is not alterable with facility to consequently cause considerable labor and increased cost in production.

Therefore, the latter method carried out with current on-time control is adopted more frequently. In general, an LED array head employed in the latter has a driving controller comprising a current on-time control circuit, an allotter circuit and a driving circuit. The on-time control circuit and the allotter circuit are formed separately from the head and are connected thereto by means of flat cables. Meanwhile the driving circuit is incorporated in the head and is formed into an IC configuration.

The current on-time control circuit serves to convert input serial data into parallel data and has an on-time compensational data memory ROM for compensating any variation in the LED-array output power. In the ROM is stored current on-time data representing the individual luminous intensities with respect to the entire bits of the LED array. Since such on-time data is determined from the luminous intensity of each bit obtained by actual measurement after complete assembly of the LED array head, composite compensation is performed inclusive of the nonuniformity of light transmitting elements as well. The allotter circuit serves to distribute the data to the integrated driving circuit related to the individual LEDs.

There are known two modes for executing such current on-time control. In the first mode, a one-line scanning time T is uniformly divided by the number m of steps, and a current is applied to each of the LED array elements for an on-time which is equal to an integral multiple of one minimum on-time unit $\Delta t$ of each step thus divided. That is, the current on-time for any LED array element producing a smaller output power is changed to be longer than the on-time for the other LED array element producing a greater output power, whereby the luminous energies of the individual LED array elements are rendered uniform to consequently compensate the luminous energy variation.

Meanwhile in the second mode, a common current on-time $T_0$ is set so that the entire LED array elements in one line are energized to emit light. And the time obtained by subtracting the common on-time $T_0$ from the one-line scanning time T is uniformly divided by the number n of steps. And the luminous energy variation is compensated by the application of a current to any LED array element, which is producing a smaller output power, for a time equal to an integral multiple of the divided fundamental on-time unit t.

The current on-time $\tau$ determined for each element according to the compensational data is expressed as $$\tau(k) = T_0 + (n-k)t$$

where
$T_0$: common current on-time
n: number of compensation steps
t: fundamental on-time unit for compensation
k: $=0, 1, 2, \ldots, n$ However, if the numbers m and n of steps are small in the current on-time control mentioned above, it is impossible to attain sufficient compensation effects for variation in the LED array elemenets; while if such numbers of steps are great, the compensational data come to increase with another problem that the composite luminous energy or output power of the entire elements is reduced by such compensation.

SUMMARY OF THE INVENTION

It is an object of the present invention to provide a method and an apparatus for compensation of LED-array output power variation in electrophotographic printing, wherein the time for applying a current to one line of the LED array is optimally divided into a fundamental on-time for constant current application to the individual elements of the LED array and a compensational on-time for selective current application thereto.

Another object of the invention resides in providing a method and an apparatus adapted to reduce the number of compensational data in compensation of LED-array output power variation.

And a further object of the invention is to provide a method and an apparatus capable of minimizing the reduction of luminous energy in compensation of LED-array output power variation.

BRIEF DESCRIPTION OF THE DRAWINGS

Many other objects of the present invention and various advantages thereof will be fully understood from the detailed description that will be given below with reference to the accompanying drawings, in which.

DETAILED DESCRIPTION OF THE PREFERRED EMBODIMENT

Hereinafter a preferred embodiment of the present invention will be described with reference to the accompanying drawings.

Figure 1:
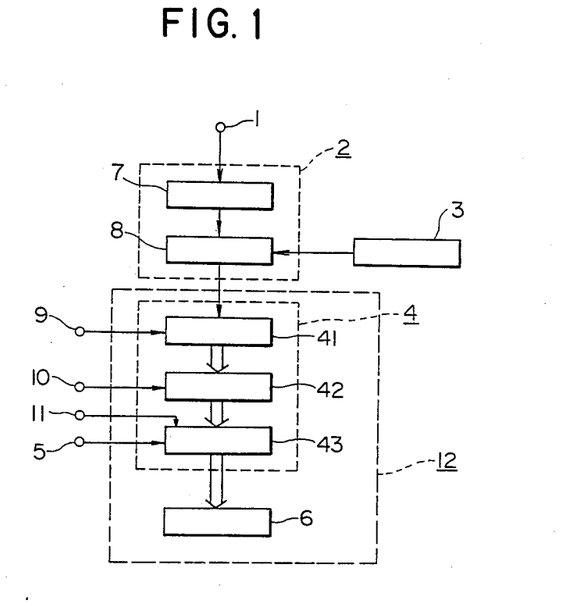
FIG. 1 is a schematic block diagram showing a preferred embodiment of the present invention designed to carry out the compensation of LED-array output power variation in electrophotographic printing.

FIG. 1 is a block diagram of an apparatus contrived to carry out the method of the invention for compensating LED-array output power variation. There are shown a picture signal input terminal 1; a circuit 2 for compensating variation in the output power or luminous energy of an LED array 6; a ROM 3 for storing compensational data fed to the compensating circuit 2; a driving circuit 4 for controlling the on-time of a current applied to the LED array 6; a power input terminal 5; a line memory 7 incorporated in the compensating circuit 2 and serving to store the picture data received from the terminal 1; a logic gate 8 for controlling the picture data of the line memory 7 in combination with the compensational data read out from the ROM 3; a CLK (clock) signal input terminal 9; a STB (strobe) signal input terminal 10; an ENB (enable) signal input terminal 11; and an LED array head 12 composed of an S/P (serial/parallel) circuit 41, a latch circuit 42, a driver circuit 43 and the LED array 6.

In the apparatus of the above constitution designed for carrying out the method of this invention to compensate any variation in the output power or luminous energy of the LED array, its operation is performed in the following manner.

First, the picture signal from the terminal 1 is stored in the line memory 7 incorporated in the compensating circuit 2 and is read out therefrom a plurality of times during a period of one-line scanning. The picture data stored in the line memory 7 is combined by the logic gate 8 with the compensational data from the ROM 3 to become a compensated picture signal, which is then fed to the LED array head 12.

Figure 2:
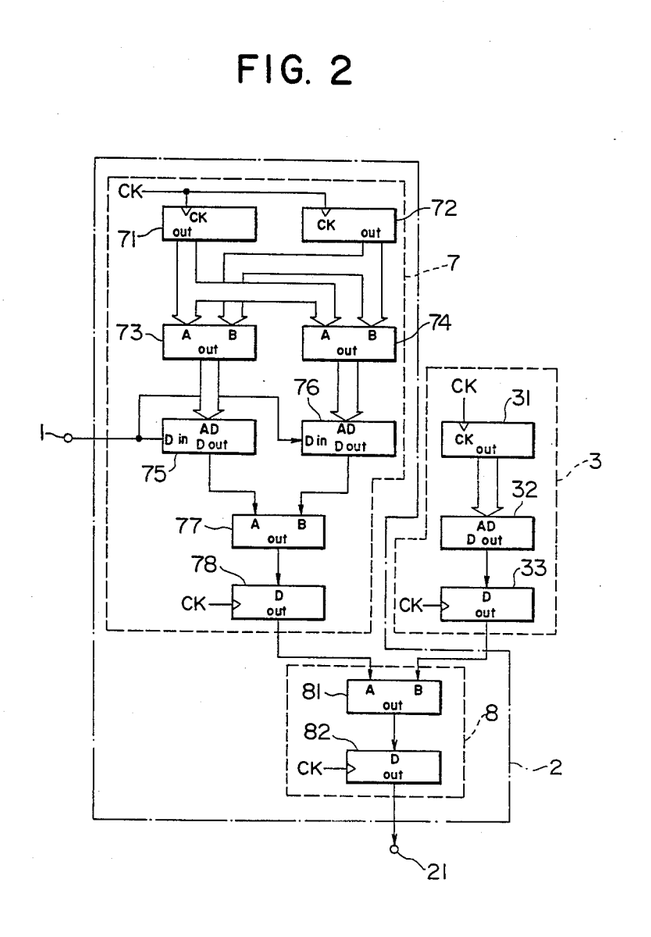
FIG. 2 is a detailed diagram of a compensating circuit employed in FIG. 1.
Figure 3:
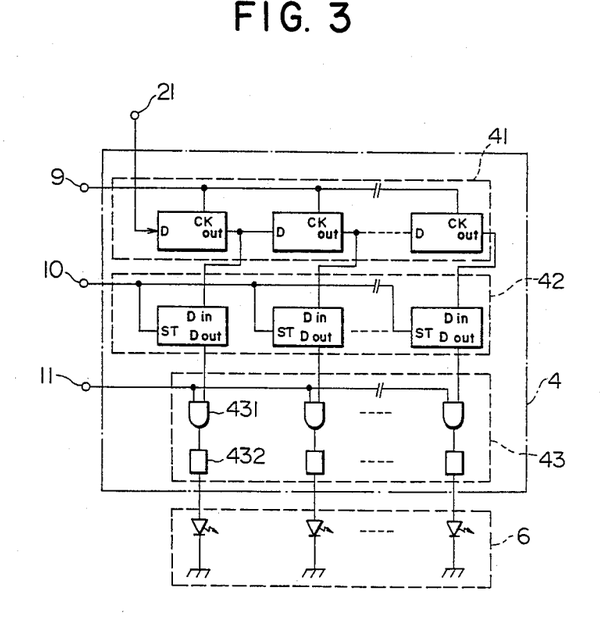
FIG. 3 is a detailed diagram of an LED array head employed in FIG. 1.

FIG. 2 is a detailed diagram of the compensating circuit 2 shown in FIG. 1, wherein a RAM read signal generated from a RAM read counter 71 and a RAM write signal from a RAM write counter 72 are selected by means of selectors 73 and 74 respectively and then are fed alternately to RAMs 75 and 76. Meanwhile the picture signal from the input terminal 1 is fed also to the RAMs 75 and 76, so that reading and writing are performed alternately in the RAMs 75 and 76. Of the output data from the RAMs 75 and 76, the signal from the RAM in its read mode is selected by a selector 77, and thus the data are outputted continuously without any interruption. The output of the selector 77 is synchronized by a D-type flip-flop 78 and then is fed to a logic gate 81. In the meantime a ROM read signal generated from a ROM read counter 31 is fed to a ROM 32, which produces output compensational data corresponding to the picture data. The compensational data is synchronized by a D-type flip-flop 33 and then is fed to the logic gate 81 together with the output of the aforesaid D-type flip-flop 78 to become new picture data including the compensational data. The picture data thus obtained from the logic gate 81 is synchronized through another D-type flip-flop 82 and then is sent to a picture data output terminal 21. The picture data from the terminal 21 is further fed to an S/P circuit 41 shown in FIG. 3 so that serial-to-parallel conversion is executed in response to a clock signal from a CLK input terminal 9. Subsequently the converted data is held by a latch circuit 42 while being triggered by a strobe signal from an STB input terminal 10 and then is passed through an AND gate 431, whereby a constant current is applied to each element of of the LED array 6 from a constant current driver 432. And a signal received from an ENB signal input terminal 11 enables a current switching action to the LED array 6.

Figure 4:
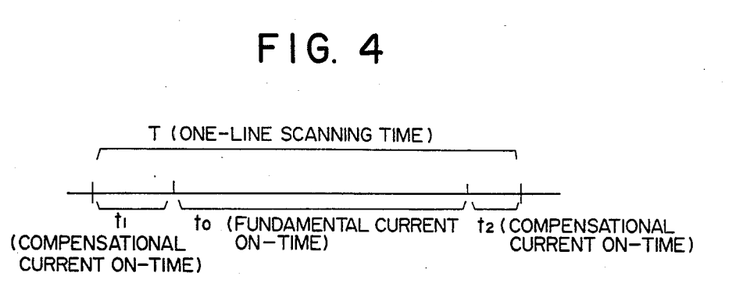
FIG. 4 is an explanatory diagram relative to division of a current on-time implementing the novel concept of the present invention.

Referring now to FIG. 4, an explanation will be given on the principle of this invention for compensating any variation that occurs in the output power or luminous energy of the LED array. In the compensation of, for example, ±40 percent luminous energy variation to ±10 percent variation, it is necessary to optimally divide the one-line scanning time T into a fundamental on-time $t_0$ for application of current in common to the entire LED array elements and compensational on-times $t_1$ and $t_2$ (number of compensation steps n=2) for selective application of current thereto. For the purpose of compensating ±40 percent variation to ±10 percent variation in this example, 0.55·T is allotted to the fundamental current on-time $t_0$ while 0.31·T and 0.14·T are allotted respectively to the two compensational current on-times $t_1$ and $t_2$ according to a calculation formula which will be described later. In the conventional current on-time control method based on uniform division, the compensational current on-time is divided uniformly by the number of steps to obtain a basic time unit for compensation, and its integral multiple is set as a current on-time. Therefore the fundamental current on-time $t_0'$ is 0.5·T as a result of calculation. Consequently, due to optimal division of the one-line scanning time T, the fundamental current on-time $t_0$ becomes 1.1 times ($t_0/t_0'$) as compared with the on-time in the conventional example, and thus the entire luminous energy also becomes about 1.1 times. Furthermore, in contrast with the conventional example where four steps are required for compensation, the number n of steps in the present invention is reduced to a half, and accordingly the number of compensational data is also reduced to a half to eventually realize a data reduction of 8K bits.

Figure 5:
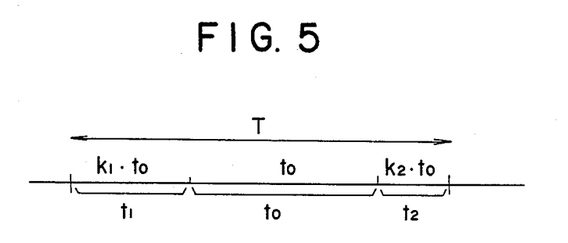
FIG. 5 shows how the current on-time is divided for compensation of LED-array output power variation in the preferred embodiment of the invention.
Figure 6:
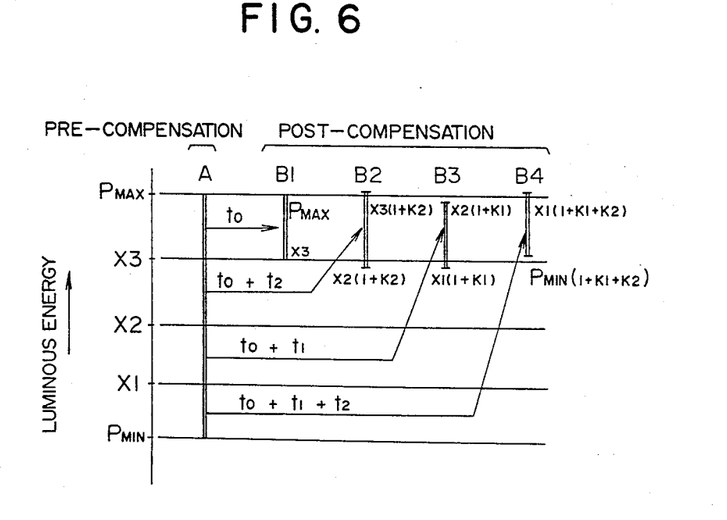
FIG. 6 graphically shows how division of the current on-time is optimized in the compensation.

Hereinafter a further explanation will be given with reference to FIGS. 5 and 6 on how to calculate the fundamental current on-time $t_0$ and the compensational current on-times $t_1$ and $t_2$ in the embodiment of the present invention. First, as shown in FIG. 5, the compensational current on-times $t_1$ and $t_2$ in the one-line scanning time T are assumed respectively as $t_1 = K1 \cdot t_0$ and $t_2 = K2 \cdot t_0$ (where $K1 > K2$). Also as shown in FIG. 6, there exist four combinations of current on-times as $t_0$, $t_0 + t_1$, $t_0 + t_2$, and $t_0 + t_1 + t_2$ with regard to the maximum value Pmax and the minimum value Pmin of the pre-compensation luminous energy of each LED array element, and three threshold levels X1, X2 and X3 (where $Pmin < X1 < X2 < X3 < Pmax$). Therefore, when the pre-compensation luminous energy of an arbitrary LED array element is Pi, the current on-time $t_i$ for that element after compensation of its luminous energy is expressed as $$t_i = t_0 \text{ if } X3 < Pi \leq Pmax$$

$$t_i = t_0 + t_2 = t_0(1 + K2) \text{ if } X2 < Pi \leq X3$$

$$t_i = t_0 + t_1 = t_0(1 + K1) \text{ if } X1 < Pi \leq X2$$

$$t_i = t_0 + t_1 + t_2 = t_0(1 + K1 + K2) \text{ if } Pmin < Pi \leq X1$$

In case the pre-compensation luminous energy distribution A is decomposed after compensation into four luminous energy distributions B1, B2, B3 and B4, optimal compensation of the luminous energy variation is achieved when coincidence is attained among the four post-compensation luminous energy distributions B1, B2, B3 and B4. Such optimal compensation can be calculated from the following simultaneous equations:

$$\begin{cases} Pmax = X3(1 + K2) = X2(1 + K1) = X1(1 + K1 + K2) \\ X3 = X2(1 + K2) = X1(1 + K1) = Pmin(1 + K1 + K2) \end{cases}$$

The current on-times $t_0$, $t_1$ and $t_2$ can be obtained by computing the approximate solutions of such simultaneous equations. Accordingly, it becomes possible to set the optimally divided fundamental on-time and compensational on-time.

Although in the above simultaneous equations the optimal compensational on-times $t_1$ and $t_2$ are determined by attaining a coincidence between the maximum and minimum values of each luminous energy distribution, the same result is obtainable by some other method as well. For example, the optimal compensational on-time can be determined by computing such approximate solutions that the difference between the maximum value Bmax and the minimum value Bmin is minimized in the aforesaid four post-compensation luminous energy distributions B1, B2, B3 and B4.

Figure 7:
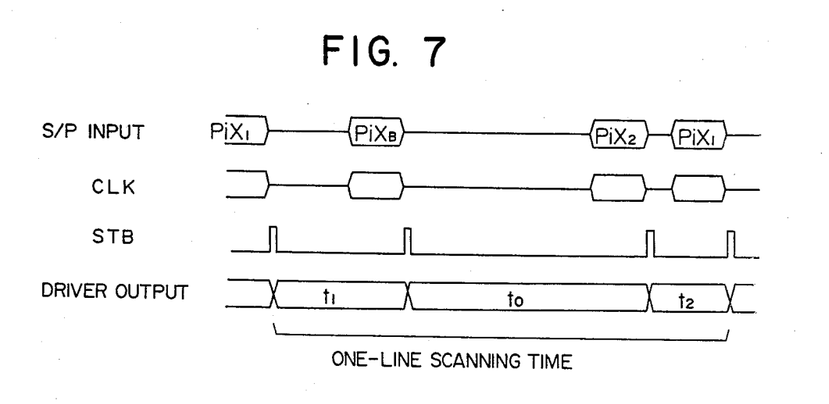
FIGS. 7 and 8 are timing charts of control signals produced for the compensation.

As for the operation performed in the LED array head 12, first the input picture data is processed through serial-to-parallel conversion by the S/P circuit 41 in response to the clock signal from the CLK input terminal 9. Then the signal from the S/P circuit 41 is latched by the latch circuit 42 in response to the strobe signal from the STB input terminal 10, and the supply power from the power input terminal 5 is controlled in the associated driver circuit 43, so that the current is applied selectively to the LED array 6. FIG. 7 is a timing chart of signals fed to the individual input terminals, wherein there are shown picture data PiX1 for the region of compensational on-time $t_1$ in FIG. 1, picture data PiXB for the region of fundamental on-time, and picture data PiX2 for the region of compensational on-time $t_2$. During the one-line scanning time, three-line picture data (PiX1, PiXB, PiX2) are supplied to the S/P circuit and serial-to-parallel conversion is executed in response to the clock signal in such a manner that after conversion of one-line picture data, no clock signal is inputted until the next picture data is received. And posterior to such serial-to-parallel conversion, the data is latched in response to the strobe signal. Therefore, by setting the strobe signal input intervals as $t_1$, $t_0$ and $t_2$, the time of current application from the driver circuit to the LED array can be divided into $t_1$, $t_0$ and $t_2$.

Figure 8:
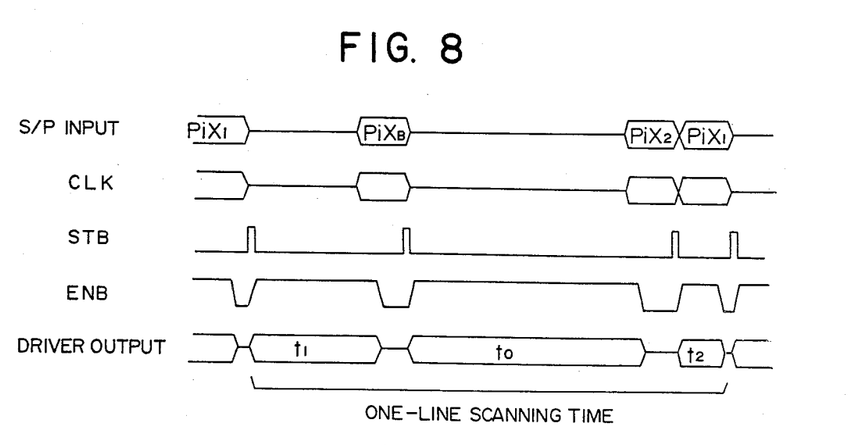

Control of the driver circuit 43 may be performed by the use of enable signal as shown in the timing chart of FIG. 8. Although in the above embodiment the description has been given on an exemplary case of compensating ±40 percent luminous energy variation to ±10 percent variation, similar effect is achievable with respect to any other variation rate also.

It is to be understood that, in addition to the most preferred embodiment of the present invention described hereinabove, various changes and modifications may be made for other embodiments as well without departing from the spirit and scope of the invention defined in the appended claims.

What is claimed is:

1. A method of compensating any variation in LED-array output power by controlling a current on-time for individual LED array elements in such a manner that the exposure values thereof on a photosensitive medium become uniform, said method comprising: determining a current on-time relative to one line of the LED array by setting a fundamental on-time for constant current application to the individual LED array elements and at least one compensational on-time for selective current application thereto; dividing the luminous energy distribution of said LED array into $2^n$ parts where n represents the set number of the compensational on-time; and attaining a coincidence between the maximum and minimum luminous energies in each of the divided $2^n$ parts of said luminous energy distribution.

2. An apparatus for carrying out the method defined in claim 1, wherein picture data is stored in a line memory and, during a one-line scanning operation, the picture data is read out a number of times equal to the set number of said fundamental current on-time and compensational current on-time.

3. An apparatus for carrying out the method defined in claim 1, wherein said compensational current on-time is controlled in accordance with compensational data stored in a ROM.

4. An apparatus for carrying out the method defined in claim 1, wherein the time of current application from a driver circuit to the LED array is divided in response to a STB (strobe) signal fed to a latch circuit.

5. An apparatus for carrying out the method defined in claim 1, wherein the time of current application from a driver circuit to the LED array is controlled by the use of an ENB (enable) signal fed to said driver circuit.

6. A method of compensating any variation in LED-array output power by controlling a current on-time for individual LED array elements in such a manner that the exposure values thereof on a photosensitive medium become uniform, said method comprising: determining a current on-time relative to one line of the LED array by setting a fundamental on-time for constant current application to the individual LED array elements and at least one compensational on-time for selective current application thereto; dividing the luminous energy distribution of said LED array into $2^n$ parts where n represents the set number of the compensational on-time; and minimizing the difference between the maximum and minimum values in the entire $2^n$ parts of the luminous energy distribution.

7. An apparatus for carrying out the method defined in claim 6, wherein picture data is stored in a line memory and, during a one-line scanning operation, the picture data is read out a number of times equal to the set number of said fundamental current on-time and compensational current on-time.

8. An apparatus for carrying out the method defined in claim 6, wherein said compensational current on-time is controlled in accordance with compensational data stored in a ROM.

9. An apparatus for carrying out the method defined in claim 6, wherein the time of current application from a driver circuit to the LED array is divided in response to a STB (strobe) signal fed to a latch circuit.

10. An apparatus for carrying out the method defined in claim 6, wherein the time of current application from a driver circuit to the LED array is controlled by the use of an ENB (enable) signal fed to said driver circuit.

* * * * *